United States Patent
Corrales

(10) Patent No.: US 6,525,238 B2
(45) Date of Patent: Feb. 25, 2003

(54) SINGLE USE DISPOSABLE SKIN AND CUFF PROTECTOR

(76) Inventor: Eva Sanchez Corrales, 11800 SW. 18th St., Apt. 408, Miami, FL (US) 33175

( * ) Notice: Subject to any disclaimer, the term of this patent is extended or adjusted under 35 U.S.C. 154(b) by 0 days.

(21) Appl. No.: 09/965,436

(22) Filed: Sep. 27, 2001

(65) Prior Publication Data

US 2002/0103450 A1 Aug. 1, 2002

Related U.S. Application Data

(60) Provisional application No. 60/265,037, filed on Jan. 30, 2001.

(51) Int. Cl.$^7$ .................................. A61F 13/00
(52) U.S. Cl. .................. 602/41; 128/686; 606/201; 606/202; 606/203
(58) Field of Search .............. 602/41–47; 128/851, 128/900, 686; 600/490, 499; 606/201–203

(56) References Cited

U.S. PATENT DOCUMENTS

| | | | |
|---|---|---|---|
| 3,473,525 A | | 10/1969 | Hanafin ..................... 128/2.05 |
| 3,606,880 A | | 9/1971 | Ogle ..................... 128/2.05 C |
| D224,812 S | | 9/1972 | Hudspith ..................... D83/12 |
| 3,757,772 A | * | 9/1973 | Goldblat et al. ............. 600/499 |
| 3,773,036 A | | 11/1973 | Weyer ................... 128/2.05 C |
| 3,930,506 A | * | 1/1976 | Overend ..................... 128/325 |
| 4,314,415 A | * | 2/1982 | De Woskin ..................... 40/21 |
| 4,967,758 A | | 11/1990 | Masciarotte ................ 128/686 |
| 5,228,448 A | * | 7/1993 | Byrd ........................... 128/677 |
| 5,251,646 A | | 10/1993 | Bowen ....................... 128/878 |
| 5,392,782 A | | 2/1995 | Garrett ....................... 128/686 |
| D356,155 S | | 3/1995 | Caven ....................... D24/165 |
| 5,396,894 A | | 3/1995 | Eide et al. .................. 128/686 |
| 5,411,518 A | | 5/1995 | Goldstein et al. ........... 606/202 |
| 5,511,552 A | | 4/1996 | Johnson ..................... 128/686 |
| 5,513,643 A | * | 5/1996 | Suite ........................ 128/686 |
| 5,620,001 A | | 4/1997 | Byrd et al. ................. 128/686 |
| 5,651,368 A | | 7/1997 | Napolitano et al. ......... 128/677 |
| 5,660,182 A | | 8/1997 | Kuroshaki et al. .......... 128/686 |
| 5,669,390 A | | 9/1997 | McCormick et al. ....... 128/686 |
| 5,678,558 A | | 10/1997 | Johnson ..................... 128/686 |
| 5,690,672 A | | 11/1997 | Cohen ....................... 606/203 |
| 5,746,213 A | * | 5/1998 | Marks ....................... 600/499 |
| 5,785,354 A | * | 7/1998 | Haas ........................... 283/74 |
| 5,797,851 A | | 8/1998 | Byrd ........................ 600/499 |
| 5,819,739 A | | 10/1998 | Levavi et al. .............. 128/686 |
| 5,842,996 A | | 12/1998 | Gruenfeld et al. .......... 600/490 |
| 5,865,761 A | | 2/1999 | Inukai et al. ............... 600/513 |
| 5,904,655 A | | 5/1999 | Brackett ................... 600/490 |
| D417,002 S | | 11/1999 | Scott ....................... D24/165 |

* cited by examiner

Primary Examiner—Nicholas D. Lucchesi
Assistant Examiner—Lalita M. Hamilton
(74) Attorney, Agent, or Firm—Holland & Knight LLP

(57) ABSTRACT

A single use disposable skin and cuff protector in the form of a wrap for surrounding at least a portion of a limb of a patient allows a sphygmomanometer cuff to be applied over the wrap. To prevent spreading of pathogens, the wrap includes a sheet having a non-porous barrier layer and optionally, an absorbent layer. The wrap is secured by a non-reusable fastener which cannot be released once fastened or once fastened, cannot be re-fastened. A line of weakening formed in the sheet facilitates removal of the wrap after use. Once secured to a patient for use, the sheet either must be severed to be removed and/or the re-usable fastener cannot be re-fastened thus preventing re-use.

9 Claims, 2 Drawing Sheets

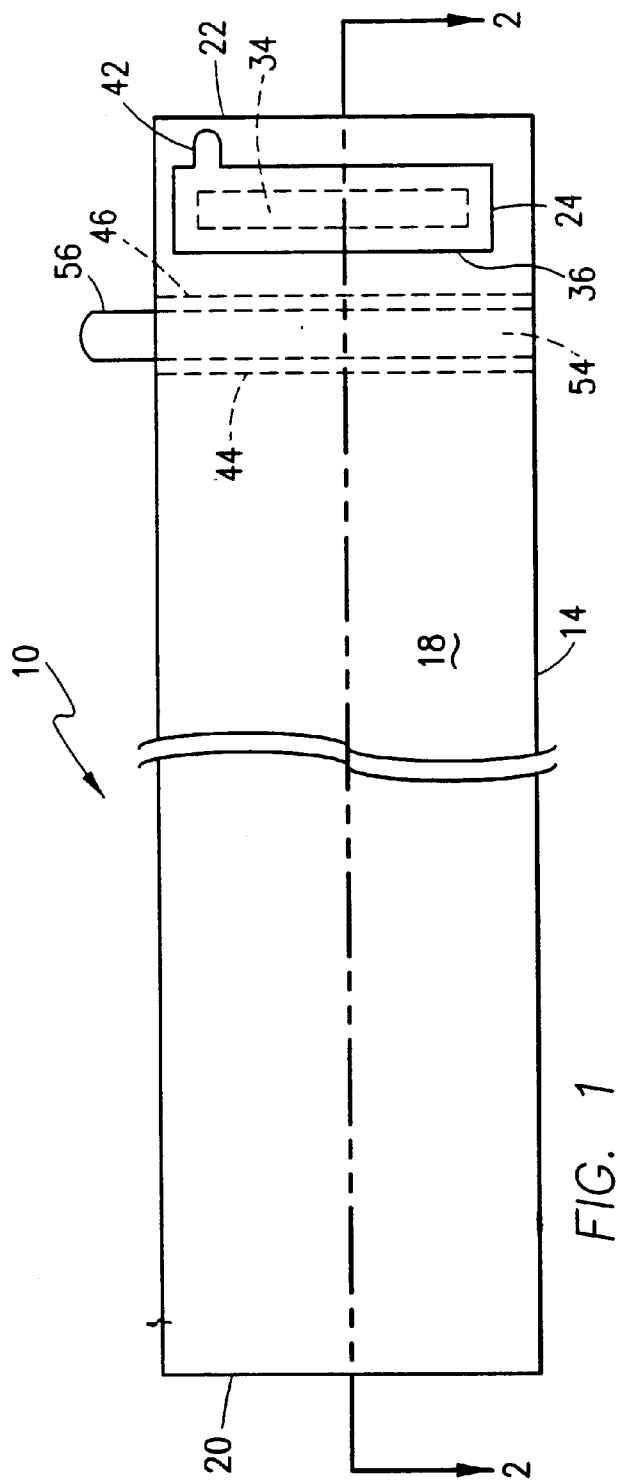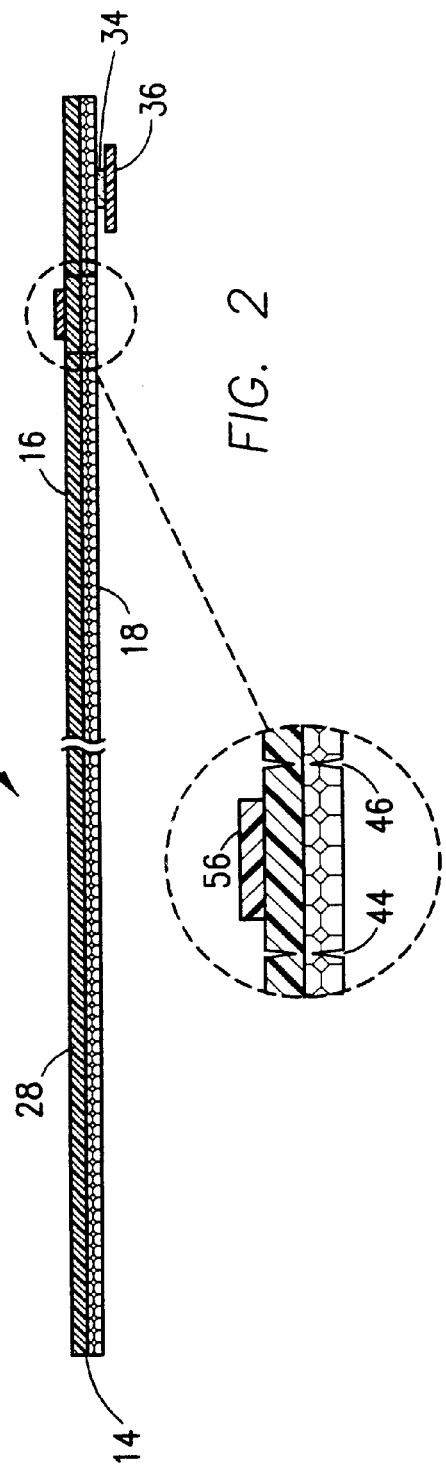

SINGLE USE DISPOSABLE SKIN AND CUFF PROTECTOR

This application claims priority under 35 U.S.C. §119(e) to U.S. Provisional Patent Application Ser. No. 60/265,037 filed Jan. 30, 2001 and entitled: "DISPOSABLE SKIN & CUFF PROTECTOR (DSCP)" which is expressly incorporated herein by reference in its entirety to form part of this application.

FIELD OF THE INVENTION

The invention relates to the field of healthcare. More particularly, the present invention relates to a DISPOSABLE protective wrap which can be secured to the upper arm of a patient to prevent transfer of pathogens between a blood pressure cuff and the patient, and which is severed or otherwise disabled in the process of removal to assure the wrap is not reused.

BACKGROUND OF THE INVENTION

Transfer of pathogens patients and devices used for medical diagnosis or treatment is both a longstanding and resurgent concern among healthcare professionals. Bacteria such as streptococcus are not only infectious but are increasingly prevalent in forms which are resistant not only to antibiotics but also to antimicrobials of the type relied on to disinfect surfaces. HIV and blood borne pathogens such as HCV (hepatitis-C) may be capable of remaining virulent for significant periods of time after having been deposited, by blood spatter or otherwise, onto surfaces outside the body. Effective prevention of cross-contamination and spread of these and other disease causing agents, particularly in a hospital or other clinical setting, requires scrupulous attention and is crucial to the well being of patients and staff alike.

It has been recognized in the prior art that the inflatable cuffs of the ubiquitous sphygomomanometer or "blood pressure cuff" used for measuring blood pressure have significant potential to serve as a vehicle for inadvertent transfer of pathogens from one person to another. Blood pressure cuffs are traditionally re-used many times in care of multiple patients and do not lend themselves to decontamination. A variety of approaches have been proposed in the prior art to prevent blood pressure cuffs from serving as a vehicle for the transfer of pathogens.

Premature infants have been recognized to be among those at acute risk of becoming infected by pathogens transferred via a sphygmomanometer. Accordingly, disposable sphygmomanometers have been developed and used while these infants are hospitalized. However, disposable sphygmomanometers are expensive and as a result not generally used in the cause of follow-up care after discharge from the hospital.

Another approach has been to manufacture only the cuff portion of the sphygmomanometer, a disposable article. For example, U.S. Pat. No. 5,678,558 to Johnson discloses a disposable blood pressure cuff intended for use only on a single patient. Other examples of disposable cuffs are shown in U.S. Pat. No. 3,473,525 to Hanafin; U.S. Pat. No. 3,757,772 to Goldblat et al. and U.S. Pat. No. 5,396,894 to Eide et al. Though intended to be inexpensive, these disposable cuffs are reasonably complex and would not be a trivial matter to manufacture economically in large numbers. Moreover, most patients have their blood pressure taken at least once and often multiple times during every visit to a physician and often many times during a single hospital stay. Disposal of the entire cuff seems wasteful and would generate a considerable bulk of material whose proper disposal as biohazardous waste would not be inexpensive. Though intended and perhaps even labelled as disposable, the structure of such cuffs does not preclude the possibility of their re-use.

Rather than fabricating the blood pressure sphygmomanometer or its cuff as a disposable article, it has also been proposed in the prior art to provide structurally simpler and less expensive and bulky disposable article to serve as a physical hygienic barrier between the patient and an otherwise conventional blood pressure cuff. Typically, these disposable barriers consist of at least one layer of non-porous plastic sheeting to block the passage of pathogens and body fluids, which may carry them. In some instances one or more layers of a non-woven or other absorbent material is provided on the side of the article which faces the patient in use. Such a layer serves both to improve patient comfort and to absorb and retain blood or sweat thus reducing the possibility of contaminant leakage. Various forms of such protective barriers are known in the prior art.

U.S. Pat. No. 5,669,390 to McCormick et al. discloses a disposable protective barrier in the form of a tubular sleeve of fluid impervious material into which the arm of the patient is inserted to above the elbow. Once the sleeve is in place, the blood pressure cuff can be applied over the lower end of the sleeve in the usual way. Afterward, the upper end of the tubular sleeve is then drawn down over the cuff to cover it prior to use. Although tubular sleeves of this type would be relatively simple to manufacture, applying them to the arm of an unconscious or struggling patient might be difficult and relatively slow. These drawbacks could be particularly problematic in an emergency setting in which even a few seconds delay could be critical to the well being of the patient.

Rather than a tubular sleeve, certain types of protective barriers in the form of a sheet of material, which wraps around the upper arm and is affixed there by detachable fasteners are also known in the prior art. For example, U.S. Pat. No. 5,513,643 to Suite shows a protective wrap in the form of a sheet having a layer of polyethylene or other non-porous material which may be overlaid with a liquid absorbing layer to be deposed facing the skin of the patient for comfort and absorbing blood or other contaminants. Mating strips of hook and loop type fastener material are disposed near opposite ends of the sheet on opposing faces of the sheet. These strips are fastened together when the sheet is wrapped around the upper arm. After the wrap is secured to the arm of the patient, a blood pressure cuff is applied over the sheet and a blood pressure reading taken in the conventional way. Once the reading is completed, the blood pressure cuff is removed and the sheet is removed by detaching the hook and loop fasteners and unwrapping it.

Protective barriers of the wrap around type just described are easy to apply even to an unconscious or uncooperative patient and are capable of providing an effective barrier to pathogens. However, though they may be manufactured in a disposable or single use form and perhaps even labeled such and provided with instructions for single use, the physical structure of these articles provides no affirmative assurance that they will not be re-used and thus rendered ineffective for their intended hygienic purpose. Since the fasteners associated with all prior art wrap around barriers for use under a blood pressure cuff of which Applicant is aware can be fastened and unfastened as many times as desired. The sleeve type barriers and "disposable" cuffs described above suffer from the same drawback. Their physical structures do not preclude the possibility of their re-use. As a result these devices may become vehicles for the transfer of pathogens from one person to another.

Since even disposable articles can be costly, especially when used in large numbers, a financial incentive to re-use such articles may exist if re-use is possible. There is also a possibility that re-use could occur inadvertently especially in a trauma center or hospital emergency room where several patients are typically under the care of overlapping or different teams of health care specialists working simultaneously in relatively small treatment areas.

Accordingly, there is a need for a protective wrap for use with a blood pressure cuff which is not only effective as a barrier to pathogens, but also provides assurance that the wrap cannot be used again once it has been used on a single occasion.

There is also a need for a protective wrap which not only provides an effective pathogen barrier and can be used only once but which is also able to be applied and removed from a patient quickly and easily.

There also exists a need for a single-use protective wrap which not only provides all of the characteristics just mentioned, but which may also include a layer of absorbent material to enhance patient comfort as well as to absorb blood or other fluids which might otherwise spread pathogens.

SUMMARY OF THE INVENTION

The invention provides a disposable protective wrap for a blood pressure cuff in the form of a sheet of material which can be wrapped at least once around the upper arm of the patient and secured in place using a fastener of a type, which once fastened, cannot be released while remaining in a condition to be fastened again on a subsequent occasion. This provides a positive assurance that the same wrap, once it is removed, will not be re-used and thus, pose a risk of spreading disease from one patient or staff member to another.

In a preferred embodiment, a disposable protective wrap to be interposed between the upper arm of a patient and a blood pressure cuff in accordance with the invention includes a flexible sheet having at least one layer of non-porous barrier material such as a plastic film. Optionally, one or more additional layers,such as a layer of absorbent woven or non-woven material facing the skin of the patient when the wrap is in use, may also be provided for comfort and absorbency. As noted above, a disposable wrap according to the present invention also includes at least one non-reusable fastener to secure the wrap in place once it has been wrapped around the upper arm of the patient. Though any known type of non-reusable fastener may be used, in a particularly preferred form of the invention the non-reusable fastener comprises at least one area of adhesive, preferably a strong, pressure sensitive adhesive applied to the body of the wrap near one end thereof and overlaid by a release backing. The release backing preferably includes a tab to facilitate its removal to expose the adhesive and allow the wrap to be adhesively secured to itself to hold it in place after having been wrapped around the limb of a patient. A blood pressure cuff can then be applied overlying the wrap and a blood pressure reading taken in the conventional way with the wrap beneath the cuff providing a barrier to transfer of pathogens between the patient and the cuff. In the preferred embodiment, the adhesive preferably creates a bond whose strength exceeds the tear strength of the body of the wrap. Thus, in order to remove the wrap from the arm of the patient, the body of the wrap must be severed, rendering the wrap incapable of re-use.

To facilitate removal, the invention contemplates providing one or more lines of weakening, such as a series of perforations, across the width of the wrap. These permit the wrap to readily be severed either by slipping a finger beneath them and pulling or by exerting tension on an optional tab. Such a tab may be formed as a projecting portion of one or more layers of the wrap or may take the form of piece of material secured to one or more of the layers of the sheet, which makes up the body of the wrap. Alternatively or in addition to one or more lines of weakening, a strap of strong paper-like or plastic material that is stronger than the sheet material of the body of the wrap is secured across the width of the wrap with sufficient bond strength to cause the sheet to tear across substantially its entire width when the strap is pulled away. It will be appreciated that the protective wrap of the invention can be manufactured economically and in large quantities using a continuous in-line manufacturing process fed by rolls of sheet material of indeterminate length with mutually adjacent wraps separated from one another by perforated lines at the ends of the wraps. After manufacturing has been completed, adjacent wraps may be separated and packed in stacks or may remain joined separably to one another along the perforated lines just mentioned and packaged in rolls. Individual units may be dispensed at the point of use using conventional dispensing containers or dispensing devices.

These and other objects and advantages of the present invention will be made even more clear to a person of ordinary skill in the art in light of the appended drawings in which like reference numerals denote like items.

BRIEF DESCRIPTION OF THE DRAWINGS

FIG. 1 is a plan view of a preferred embodiment of a single use protective wrap in accordance with the invention;

FIG. 2 is a cross-sectional view taken along line 2—2 of FIG. 1, and

DETAILED DESCRIPTION

Figure 3:
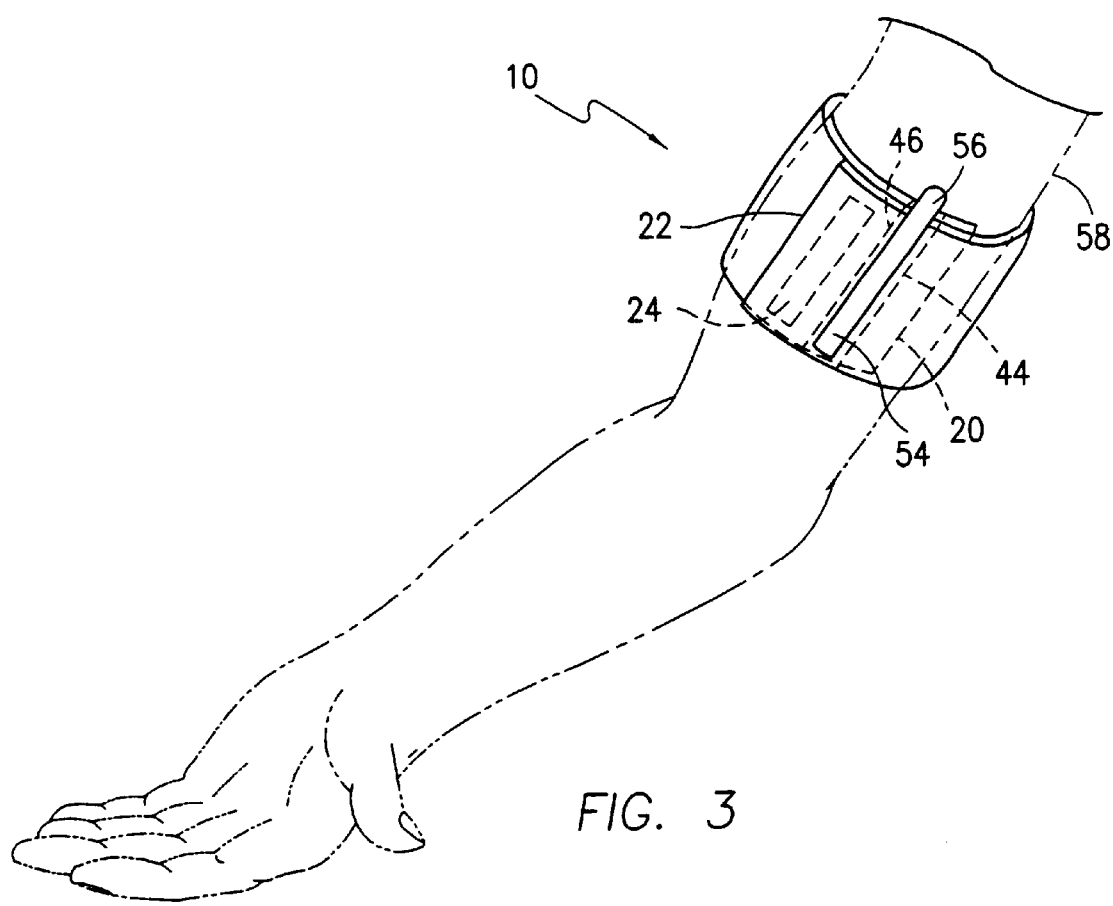
FIG. 3 is an illustration showing the protective wrap of FIG. 1 in use applied to the upper arm of a patient.

A preferred embodiment of a wrap 10 for providing a hygienic barrier between a patient and the inflatable cuff of a sphygmomanometer (not shown) is illustrated in FIG. 1 and FIG. 2. In this preferred embodiment wrap 10 takes the form of a generally rectangular sheet 14 which is preferably at least about two inches wider overall than the width of the blood pressure cuff to be used for a particular patient. Sheet 14 has an exterior face 16, a mutually opposed interior face 18 and a pair of ends 20 and 22. A non-reusable fastener 24 is disposed on interior face 18 at or near end 22. Sheet 14 should be long enough to wrap completely around the upper arm of the patient at least once with end 22 overlapping end 20 by a distance sufficient to permit fastener 24 to fasten securely to exterior face 16. If desired, wrap 10 may be manufactured in various sizes recognizing that for adult patients sheet 14 will be longer than required for pediatric patients. Sizes corresponding to the conventional sphygmomanometer size designations known as, "infant," "child," "adult" and "XL adult" are contemplated.

Sheet 14 should also be sufficiently thin and flexible not to interfere with blood pressure readings and may suitably comprise a sheet having one or more layers of different types of material. Whether or not it is made up of any additional layers, sheet 14 includes a non-porous barrier layer 28 of any suitable material through which bacteria or other pathogens of concern may not readily pass. Barrier layer 28 preferably comprises a layer of plastic sheeting or film which, depending on the material used, preferably ranges from about two to about twenty mils in thickness. Although a variety of materials can be used, a polyethylene film about 2 to about 10 mils thick generally will provide an adequate and inexpensive barrier layer 28. A barrier layer of about 3 to 5.5 mils of polyethylene is preferred. If no additional layers, such as an absorbent layer as described below is used, barrier layer may optionally be embossed or textured to provide improved patient comfort.

For patient comfort and absorption of body fluids, the interior face 18 of sheet 14 preferably comprises the surface of a soft woven or non-woven absorbent layer 30. Although woven fabric such as cotton or a synthetic fiber or blend could be used, absorbent layer 30 preferably comprises a non-woven material of the type commonly used in disposable diapers. Such material offers excellent absorbency, is economical and can be applied directly to barrier layer 28 a continuous in-line manufacturing process using conventional application equipment such as that available from the Non-Woven Systems Group of The Nordson Corporation of Westlake, Ohio. Absorbent layer 30 should not exceed about one eighth of an inch in thickness and is preferably about one sixteenth of an inch thick or less to avoid undue bulk for economy of packaging, shipping and storage as well as to minimize waste and disposal costs. Excessive bulk may also tend to interfere with accurate blood pressure readings.

Materials suitable for use as sheet 14 and which have a plastic barrier layer 28 already bonded to a suitable absorbent layer 30 are commercially available. An example is the material used in the disposable patient gowns that are readily commercially available from a variety of sources.

According to the invention wrap 10 includes a non-reusable fastener 24 which may suitably be located at or near the end 22 of sheet 14. As used herein and in the claims, the term "non-reusable fastener" refers to any type of fastener which either cannot be released by ordinary means once it has been fastened or which after having been fastened and released only once cannot be re-fastened by ordinary means. An adhesive that cannot be removed or which cannot be re-bonded after having once been adhered may serve as a suitable non-reusable fastener. Another familiar example of fasteners which are "non-reusable" in this sense include the highly versatile strap type fasteners such as those available under the mark TY-RAP® from Thomas & Betts Co. of Elizabeth, N.J. Snap fasteners used on hospital patient identification bracelets such as those available from Precision Dynamic Corporation of San Fernando, California cannot be released once secured and are another example of a "non-reusable" fastener which can be used.

In accordance with the preferred embodiment shown in FIGS. 1 and 2, non-reusable fastener 24 is provided in the form of a patch of pressure-sensitive adhesive 34 which is applied to the interior face 18 of sheet 14 and adhered substantially permanently thereto. Adhesive 34 is overlaid by a conventional strip of release backing 36 which preferably includes a protruding ear 42 which permits backing 36 to be easily gripped and peeled away to apply wrap 10 to a patient even if the person applying wrap 10 is wearing rubber gloves.

To facilitate removal and simultaneous severing of wrap 10 to prevent its re-use, the width of sheet 14 is preferably traversed by at least one line of weakening 44. In the preferred embodiment, a second line of weakening 46 is provided parallel to and mutually spaced about one half to one inch from line of weakening 44. In the preferred embodiment lines of weakening 44 and 46 are formed as linear arrays of closely spaced perforations which completely penetrate all of the layers of sheet 14 such that the entire zone of sheet 14 lying between lines 44 and 46 can be easily torn away to sever sheet 14 to both remove wrap 10 from the arm of a patient and at the same time, prevent wrap 10 from being re-used. Such techniques include weakening sheet 14 along a desired path across its width by applying heat, radiation or chemical agents to embrittle or weaken one or more layers of sheet 14. Those skilled in the art will appreciate that any other technique for forming a weakened area may also be used to form lines of weakening 44, 46 in addition to or in lieu of perforations.

In addition to or in lieu of one or more lines of weakening 44, 46, severing of sheet 14 may also be facilitated by a strap 54. As illustrated in FIGS. 1 and 2, strap 54 may comprise a length of material which spans all or most of the width of sheet 14. Strap 54 is permanently secured to sheet 14, preferably in the zone between lines of weakening 44 and 46, and has a free end 56 which protrudes beyond the outer edge of sheet 14 by about one half inch or more. Strap 54 can be secured to sheet 14 using a suitable adhesive or, depending on the materials involved, by solvent bonding, ultrasonic welding on other suitable bonding technique. While strap 54 is shown in FIGS. 1 and 2 as being attached to the exterior face 16 of sheet 14, strap 54 may alternatively be attached to the interior face 18 of sheet 14. Strap 54 may suitably be formed as a relatively thin rectangular strip of any non-brittle material that is sufficiently strong that by grasping and pulling on the free end 56 of strap 54 sheet 14 can be readily severed or torn completely across its entire width without undue effort. Although any number of injection molded thermoplastic materials such as polypropyline or polycarbonate could be used, strap 54 is preferably formed of a thin strip of spunbonded polyolefin sheet. One such material is that which is readily commercially available from E.I. du Pont de Nemours and Company of Wilmington, Delaware under the trademark Tyvek Mailwrap®. This material is not only economical but is also highly pliable and strong even though only a few mils thick. High pliability is desirable in order to avoid both discomfort to the patient and the possibility of creating pressure points which might interfere with accurate blood pressure readings. Pliability and thinness of strap 54 also will facilitate packaging and dispensing of wrap 10.

Rather than a rectangular strip as shown in FIGS. 1 and 2, strap 54 may alternatively take the form of a length of strong but small diameter cord or string such as a monofilament or braided fishing line (not shown). In such a form, strap 54 may be terminated at its free end 56 by being tied in a loop or attached to a plastic ring (not shown) into which a person may insert a finger to pull strap 54 in order to sever sheet 14.

In use, as illustrated in FIG. 3, wrap 10 is wrapped non-constrictively around the upper arm 54 of a patient and held in place by non-reusable fastener 24. Once non-reusable fastener 24 is fastened, the invention contemplates that, depending on the particular type of non-reusable fastener selected, the fastener either cannot be refastened once it has been released or cannot be unfastened by ordinary means. The adhesive 34 used in the preferred embodiment makes up a non-reusable fastener 24 of the latter type. Tab 38 is grasped and pulled to peel release-backing 36 free of pressure-sensitive adhesive 34. Wrap 10 is then positioned to encircle the upper arm 54 with absorbent layer 30 facing toward the skin of the patient and end 22 of sheet 14 overlapping its opposite end 20. As shown in FIG. 3, lines of weakening 44 and 46 are positioned to lie entirely within the region overlapping between ends 20 and 22 when wrap 10 is applied to the limb of the patient. Pressure sensitive adhesive 34 is then brought into contact with the exterior face 18 of sheet 14 and pressed into place to fasten 10 wrap non-reusably in place around the upper arm 54 of the patient. Once adhered, adhesive 34 bonds to barrier layer 28 substantially permanently. The bond is sufficiently strong that attempting to pull it free would instead result only in tearing (severing) sheet 14 substantially completely across its entire width thus, desirably rendering wrap 10 incapable of being re-used.

With wrap 10 so applied to the limb of the patient, the blood pressure readings may be taken in the otherwise usual manner after the inflatable cuff of a sphygmomanometer (not shown) is placed around the limb over wrap 10 such that no part of the cuff comes into direct contact with the patient. The barrier layer 28 of sheet 14 serves to prevent transfer of bacteria, viruses or other pathogens from the inflatable blood pressure cuff to the underlying skin or clothing of the patient. Barrier layer also prevents transfer of such pathogens from the skin or clothing of the patient to the cuff. In addition, optional absorbent layer 30 absorbs any blood or other body fluids which may be present on the patient to prevent them from dripping and spreading any pathogens they may contain. It will be appreciated therefore that wrap 10 not only protects the patient, but also helps to protect the is health care staff who subsequently handle the blood pressure cuff and patients on whom the same cuff may later be used.

After blood pressure measurements are taken and the inflatable cuff of the sphygmomanometer removed, wrap 10 is itself removed from the patient and in so doing, is rendered unusable. In the preferred embodiment, wrap 10 is severed completely across the width of sheet 14 so as to be rendered incapable of being re-used either unintentionally or otherwise. Removal and severing of the preferred embodiment of wrap 10 can be carried out simply by grasping the free end 50 of strap 52 and pulling strap 54 downwardly. Doing so causes lines of weakening 44 and/or 46 to part thereby severing sheet 14 completely and across its entire width. If a strap 54 is not included, sheet 14 may readily be severed by placing a finger or instrument under sheet 14 near or in the zone between lines of weakening 44 and 46 and pulling outwardly and downwardly to cause lines of weakening 44 and/or 46 to part, severing sheet 14 completely across its entire width.

Where non-reusable fastener 24 is of a type which can be fastened once but not re-fastened after having been released, it is not necessary to sever rectangular sheet 14 in order to render wrap 10 incapable of re-use. In such embodiments, re-use will be prevented by non-reusable fastener 24 itself due to its inability to be re-fastened after having once been fastened and released. In such embodiments therefore lines of weakening 44, 46 and/or strap 54 are optional but not essential.

While the foregoing constitute preferred embodiments of the present invention, it is to be understood that the invention is not limited thereto and that in light of the present disclosure, various alternative embodiments will be apparent to persons skilled in the art. Accordingly, it is to be recognized that changes can be made without departing from the scope of the invention as particularly pointed out and distinctly claimed in the appended claims which shall be construed to encompass all legal equivalents thereof.

What is claimed is:

1. A protective wrap for surrounding at least a portion of a limb of a patient for helping prevent transfer of pathogens between the patient and a blood pressure cuff applied over the wrap, said wrap comprising:
    a generally rectangular, flexible sheet having a pair of mutually spaced ends, said sheet being comprised of at least one layer located between said ends, said at least one layer including a non-porous barrier layer, said sheet being of sufficient length between said ends to wrap at least once around the circumference of the limb of the patient such that said ends overlap one another, said sheet being of a width wider than the width of the blood pressure cuff,
    a non-reusable fastener mechanically coupled to said sheet for securing said ends in overlapping relation to one another on the limb of the patient, and
    at least one line of weakening formed in every said layer of said sheet, including said non-porous pathogen barrier layer, said at least one line of weakening rendering every said layer of said sheet severable along across the entirety of said width of said sheet whereby every said layer of said sheet can be completely severed along said at least one line of weakening to completely sever said sheet across the entirety of said width of said sheet to both facilitate removal of said sheet from the limb of the patient and to reduce the risk of subsequent spread of pathogens from the wrap by preventing the wrap from being reused.

2. The wrap of claim 1 wherein said fastener comprises a pressure sensitive adhesive covered by a removable release backing.

3. The wrap of claim 1 further comprising at least one strap secured to said sheet and spanning substantially the entire said width of said sheet, said strap having a free end projecting beyond at least one edge of said sheet whereby severing of said sheet may be facilitated by grasping said free end and applying force to said strap.

4. The wrap of claim 3 wherein said strap is located adjacent said line of weakening.

5. A protective wrap for surrounding at least a portion of a limb of a patient for helping prevent transfer of pathogens between the patient and a blood pressure cuff applied over the wrap, said wrap, comprising:
    a generally rectangular flexible sheet having a pair of mutually spaced ends, said sheet being comprised of at least two layers, including a non-porous pathogen barrier layer located between said ends and an absorbent layer overlying at least a portion of said barrier layer, said sheet being of sufficient length between said ends to wrap at least once around the circumference of the limb of the patient such that said ends overlap one another and at least a portion of said absorbent layer contacts the limb of the patient, said sheet being of a width wider than the width of the blood pressure cuff,
    a non-reusable fastener mechanically coupled to said sheet for securing said ends in overlapping relation to one another on the limb of the patient, and
    at least one line of weakening formed in every said layer of said sheet, including said non-porous pathogen barrier layer, said at least one line of weakening spanning said width of said sheet to render every said layer of said sheet severable across the entirety of said width of said sheet whereby every said layer of said sheet can be completely severed along said at least one line of weakening to completely sever said sheet across the entirety of said width of said sheet to both facilitate removal of said sheet from the limb of the patient and to reduce the risk of subsequent spread of pathogens from the wrap by preventing the wrap from being reused.

6. The wrap of claim 5 wherein said fastener comprises a pressure sensitive adhesive covered by a removable release backing.

7. The wrap of claim 5 further comprising at least one strap secured to said sheet and spanning substantially the entirety of said width of said sheet, said strap having a free end projecting beyond at least one edge of said sheet whereby severing of said sheet may be facilitated by grasping said free end and applying force to said strap.

8. The wrap of claim 7 wherein said strap is located adjacent said line of weakening.

9. A protective wrap for surrounding at least a portion of a limb of a patient for helping prevent transfer of pathogens between the patient and a blood pressure cuff applied over the wrap, said wrap comprising:

a generally rectangular, flexible sheet having a pair of mutually spaced ends, said sheet being comprised of at least one layer located between said ends, said at least one layer including a non-porous barrier layer, said sheet being of a width wider than the width of the blood pressure cuff and being of sufficient length between said ends to wrap at least once around the circumference of the limb of the patient such that said ends overlap one another in an overlapping region, a non-reusable fastener mechanically coupled to said sheet for securing said ends in overlapping relation to one another on the limb of the patient, at least one line of weakening formed in every said layer of said sheet, including said non-porous pathogen barrier layer, said at least one line of weakening being located entirely within said overlapping region and being oriented across said width of said sheet to render every said layer of said sheet severable across the entirety of said width of said sheet whereby every said layer of said sheet can be completely severed along said at least one line of weakening to completely sever said sheet across the entirety of said width of said sheet to both facilitate removal of said sheet from the limb of the patient and to reduce the risk of subsequent spread of pathogens from the wrap by preventing the wrap from being reused.

* * * * *